United States Patent
Meade et al.

(10) Patent No.: US 9,045,766 B2
(45) Date of Patent: Jun. 2, 2015

(54) COMBINED USE OF VIP3AB AND CRY1AB FOR MANAGEMENT OF RESISTANT INSECTS

(75) Inventors: Thomas Meade, Zionsville, IN (US); Kenneth Narva, Zionsville, IN (US); Joel J. Sheets, Zionsville, IN (US); Nicholas P. Storer, Kensington, MD (US); Stephanie L. Burton, Indianapolis, IN (US); Aaron T. Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 541 days.

(21) Appl. No.: 13/329,013

(22) Filed: Dec. 16, 2011

(65) Prior Publication Data

US 2012/0159674 A1    Jun. 21, 2012

Related U.S. Application Data

(60) Provisional application No. 61/423,935, filed on Dec. 16, 2010.

(51) Int. Cl.
*C12N 15/82* (2006.01)
*C07K 14/325* (2006.01)
*C07K 14/32* (2006.01)

(52) U.S. Cl.
CPC ............ *C12N 15/8286* (2013.01); *C07K 14/32* (2013.01); *C07K 14/325* (2013.01)

(58) Field of Classification Search
None
See application file for complete search history.

(56) References Cited

U.S. PATENT DOCUMENTS

| | | | |
|---|---|---|---|
| 2004/0128716 | A1 | 7/2004 | Narva et al. |
| 2007/0006340 | A1 | 1/2007 | Lang et al. |

FOREIGN PATENT DOCUMENTS

| | | | |
|---|---|---|---|
| WO | WO 2005/054479 A1 | 6/2005 | |
| WO | WO 2005/103266 A1 | 11/2005 | |
| WO | WO 2007/142840 A2 | 12/2007 | |
| WO | WO 2008/080166 A2 | 7/2008 | |
| WO | WO 2009/132850 A1 | 11/2009 | |
| WO | WO 2009/149787 A1 | 12/2009 | |
| WO | WO 2011/075590 A1 | 6/2011 | |
| WO | WO 2011/084631 A1 | 7/2011 | |

OTHER PUBLICATIONS

Fang et al (2007, Appl. Environ. Microbiol. 73:956-961).*
Hofte et al (1986, Eur. J. Biochem. 161:273-280).*
Bates et al (2005, Nature Biotechnol. 23:57-62).*
Dively (2005, Environ. Entomol. 34:1267-1291).*
Estruch et al (1996, Proc. Natl. Acad. Sci, USA 93:5389-5394).*
Bravo et al., How to cope with insect resistance to Bt toxins?, Trends in Biotechnology, Elsevier publications, Cambridge, GB, vol. 26, No. 10, Oct. 2, 2008, pp. 573-579, XP025406825. *the whole document*.
Burkness et al., Novel Vip3A *Bacillus thuringiensis* (Bt) maize approaches high-dose efficacy against *Helicoverpa zea* (Lepidoptera: Noctuidae) under field conditions, GM Crops. vol. 1, No. 5, Nov. 2010. The whole document, abstract, p. 340, right-hand col. para 2.
Kurtz et al., Insect resistance management for Syngenta's VipColt(TM) transgenic, Journal of Invertebrate Pathology, San Diego, CA, US, vol. 95, No. 3, Jun. 23, 2007, pp. 227-230, XP022126995, ISSN: 0022-2011, DOI: 10.1016/J.JIP.2007.03.014.
Adamczyk, Jr. et al., Efficacy of VIP3A and CRY1AB Transgenic Traits in Cotton Against Various Lepidopteran Pests, Florida Entomologist, The Society, Winter Haven, FL, US, vol. 91, No. 4, Dec. 1, 2008, pp. 570-575, XP001539163, ISSN: 0015-4040
Roush R T: "Two-Toxin Strategies for Management of Insecticidal Transgenic Crops: Can Pyramiding Succeed Where Pesticide Mixtures Have Not?", Philosophical Transactions. Royal Society of London.Biological Sciences, Royal Society, London, GB, vol. 353, No. 1376, Oct. 29, 1998, pp. 1777-1786, XP008032212, ISSN: 0962-8436, DOI: 10.1098/RSTB.1998.0330.
Zhao Jian-Zhou et al: "Transgenic plants expressing two *Bacillus thuringiensis* toxins delay insect resistance evolution", Nature Biotechnology, Nature Publishing Group, New York, NY, US, vol. 21, No. 12, Dec. 1, 2003, pp. 1493-1497, XP002488280, ISSN: 1087-0156, DOI: 10.1038/NBT907 [retrieved on Nov. 9, 2003].
VIP Proteins, http://www.lifesci.sussex.ac.uk/home/Neil_crickmore/Bt/vip/html, dated Dec. 1, 2014.
Crickmore, et al., Revision of the Nomenclature for the *Bacillus thuringiensis* Pesticidal Crystal Proteins, Microbiology and Molecular Biology Reviews, Sep. 1998, pp. 807-813, vol. 62, No. 3.
Memorandum dated Feb. 8, 2007 from the US EPA to Mike Mendelsohn, regarding review of product characterization and human health data for plant-incorporated protectant *Bacillus thuringiensis* (Bt) VIP3Aa20 insect control protein.
Burkness E. C. et al., Novel Vip3A *Bacillus thuringiensis* (Bt) maize approaches high-dose efficacy against *Helicoverpa zea* (Lepidoptera: Noctuidae) under field conditions: Implications for resistance management., GM Crops Nov.-Dec. 2010 LNKD-PUBMED: 21844691, vol. 1, No. 5, Nov. 2010, pp. 337-343, XP002670815, ISSN: 1938-2006.

* cited by examiner

*Primary Examiner* — Anne Kubelik
(74) *Attorney, Agent, or Firm* — Ronald S. Maciak; Faegre Baker Daniels LLP (57) ABSTRACT

The subject invention includes methods and plants for controlling lepidopteran insects, said plants comprising a Vip3Ab insecticidal protein in combination with a Cry1Ab protein to delay or prevent development of resistance by the insect(s)—particularly corn earworm.

24 Claims, 2 Drawing Sheets

COMBINED USE OF VIP3AB AND CRY1AB FOR MANAGEMENT OF RESISTANT INSECTS

CROSS-REFERENCE TO A RELATED APPLICATION

The subject application claims priority to U.S. provisional application Ser. No. 61/423,935, filed on Dec. 16, 2010.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1F and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm). See also US 2009 0313717, which relates to a Cry2 protein plus a Vip3Aa, Cry1F, or Cry1A for control of *Helicoverpa zea* or *armigera*. WO 2009 132850 relates to Cry1F or Cry1A and Vip3Aa for controlling *Spodoptera frugiperda*. US 2008 0311096 relates in part to Cry1Ab for controlling Cry1F-resistant ECB.

That is, some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol*. 16:144-146).

The proteins selected for use in an IRM stack need to exert their insecticidal effect independently so that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is said to be cross-resistant to both Bt toxins. However, if two toxins bind to two different receptors, this could be an indication that the insect would not be simultaneously resistant to those two toxins.

Cry1Fa is useful in controlling many lepidopteran pests species including the European corn borer (ECB; *Ostrinia nubilalis* (Hübner)) and the fall armyworm (FAW; *Spodoptera frugiperda*), and is active against the sugarcane borer (SCB; *Diatraea saccharalis*). The Cry1Fa protein, as produced in corn plants containing event TC1507, is responsible for an industry-leading insect resistance trait for FAW control. Cry1Fa is further deployed in the Herculex®, SmartStax™, and WideStrike™ products.

Additional Cry toxins are listed at the website of the official B.t. nomenclature committee (Crickmore et al.; lifesci.sussex.ac.uk/home/Neil_Crickmore/Bt/). There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the discovery that Vip3Ab and Cry1Ab do not compete with each other for binding to gut receptors from *Helicoverpa zea* (corn earworm; CEW). The subject invention also relates in part to the surprising discovery that Vip3Ab is active against diamondback moths (DBM) that are resistant to Cry1Ab.

As one skilled in the art will recognize with the benefit of this disclosure, plants expressing Vip3Ab and Cry1Ab, or insecticidal portions thereof, will be useful in delaying or preventing the development of resistance to either of these insecticidal proteins alone.

Thus, the subject invention relates in part to the use of a Vip3Ab protein in combination with a Cry1Ab protein. Plants (and acreage planted with such plants) that produce Vip3Ab plus Cry1Ab are included within the scope of the subject invention.

The subject invention also relates in part to triple stacks or "pyramids" of three (or more) toxins, with Vip3Ab and Cry1Ab being the base pair. Such triple stacks can provide three proteins providing non-competitive action against CEW. This can help to further reduce or eliminate the requirement for refuge acreage.

BRIEF DESCRIPTION OF THE SEQUENCES

SEQ ID NO:1 is the full-length Vip3Ab protein which, as used in the binding studies, was trypsin processed to a core fragment (residues 200-788).

SEQ ID NO:2 is the full-length Cry1Ab protein which, as used in the binding studies, was trypsin processed to a core fragment (residues 29-612).

DETAILED DESCRIPTION OF THE INVENTION

The subject invention is supported in part by the discovery that Vip3Ab and Cry1Ab do not compete with each other for binding to gut receptors from *Helicoverpa zea* (corn earworm; CEW).

The subject invention includes the use of Vip3Ab and Cry1Ab to protect corn and other economically important plant species from damage and yield loss caused by CEW feeding and to prevent CEW populations from developing resistance to either of these proteins.

The present invention provides compositions for controlling lepidopteran pests comprising cells that produce a Cry1Ab core toxin-containing protein and a Vip3Ab core toxin-containing protein.

The invention further comprises a host transformed to produce both a Cry1Ab insecticidal protein and a Vip3Ab insecticidal protein, wherein said host is a microorganism or a plant cell. In some embodiments, the plant cells are non-propagating/non-totipotent cells. The subject polynucleotide(s) are preferably in a genetic construct under control of (operably linked to/comprising) a non-*Bacillus-thuringiensis* promoter. The subject polynucleotides can comprise plant codon usage for enhanced expression in a plant.

It is additionally intended that the invention provides a method of controlling lepidopteran pests comprising contacting said pests or the environment of said pests with an effective amount of a composition that contains a Cry1Ab core toxin-containing protein and further contains a Vip3Ab core toxin-containing protein.

An embodiment of the invention comprises a maize plant comprising a plant-expressible gene encoding a Vip3Ab core toxin-containing protein and a plant-expressible gene encoding a Cry1Ab core toxin-containing protein, and seed of such a plant.

A further embodiment of the invention comprises a maize plant wherein a plant-expressible gene encoding a Vip3Ab core toxin-containing protein and a plant-expressible gene encoding a Cry1Ab core toxin-containing protein have been introgressed into said maize plant, and seed of such a plant.

As described in the Examples, competitive receptor binding studies using radiolabeled Cry1Ab show that the Cry1Ab core toxin protein does not compete for binding in CEW insect tissues to which Vip3Ab binds. These results also indicate that the combination of Cry1Ab and Vip3Ab proteins is an effective means to mitigate the development of resistance in CEW populations to Cry1Ab (and likewise, the development of resistance to Vip3Ab), and would likely increase the level of resistance to this pest in corn plants expressing both proteins. Thus, based in part on the data described herein, it is thought that co-production (stacking) of the Vip3Ab and Cry1Ab proteins can be used to produce a high dose IRM stack for CEW.

Other proteins can be added to this pair to expand insect-control spectrum. Another deployment option would be to use Cry1Ab and Vip3Ab proteins in combination with another, third toxin/gene, and to use this triple stack to mitigate the development of resistance in CEW to any of these toxins. Thus, another deployment option of the subject invention would be to use two, three, or more proteins in crop-growing regions where CEW can develop resistant populations.

Accordingly, the subject invention also relates in part to triple stacks or "pyramids" of three (or more) toxins, with Cry1Ab and Vip3Ab toxins being the base pair. In some preferred pyramid embodiments, the selected proteins provide non-competitive action against CEW.

Plants (and acreage planted with such plants) that produce any of the subject combinations of proteins are included within the scope of the subject invention. Additional toxins/genes can also be added, but the particular stacks discussed above advantageously and surprisingly provide multiple modes of action against CEW. This can help to reduce or eliminate the requirement for refuge acreage. A field thus planted of over 10 acres is thus included within the subject invention.

GENBANK can also be used to obtain the sequences for any of the genes and proteins disclosed or mentioned herein.

Combinations of proteins described herein can be used to control lepidopteran pests. Adult lepidopterans, for example, butterflies and moths, primarily feed on flower nectar and are a significant effector of pollination. Nearly all lepidopteran larvae, i.e., caterpillars, feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

Some chimeric toxins of the subject invention comprise a full N-terminal core toxin portion of a Bt toxin and, at some point past the end of the core toxin portion, the protein has a transition to a heterologous protoxin sequence. The N-terminal, insecticidally active, toxin portion of a Bt toxin is referred to as the "core" toxin. The transition from the core toxin segment to the heterologous protoxin segment can occur at approximately the toxin/protoxin junction or, in the alternative, a portion of the native protoxin (extending past the core toxin portion) can be retained, with the transition to the heterologous protoxin portion occurring downstream.

As an example, one chimeric toxin of the subject invention, is a full core toxin portion of Cry1Ab (approximately the first 600 amino acids) and a heterologous protoxin (the remainder of the molecule to the C-terminus). In one preferred embodiment, the portion of a chimeric toxin comprising the protoxin is derived from another Cry1Ab protein toxin.

A person skilled in this art will appreciate that Bt toxins, even within a certain class such as Cry1A, will vary to some extent in length and the precise location of the transition from core toxin portion to protoxin portion. Typically, the Cry1Ab toxins are about 1150 to about 1200 amino acids in length. The transition from core toxin portion to protoxin portion will typically occur at between about 50% to about 60% of the full length toxin. The chimeric toxin of the subject invention will include the full expanse of this N-terminal core toxin portion. Thus, the chimeric toxin will comprise at least about 50% of the full length of the Cry1Ab Bt toxin protein. This will typically be at least about 590 amino acids. With regard to the protoxin portion, the full expanse of the Cry1Ab protoxin portion extends from the end of the core toxin portion to the C-terminus of the molecule.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Ab's and Vip3Ab's), 78% (Cry1F's and Vip3A's), and 45% (Cry1's and Vip3's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only (for Cry1Ab, for example). Proteins for use according to the subject invention can be, for example, at least 75%, 85%, 90%, 95%, or 99% (and any integer increment within this range) identical (amino acid identity) with a protein exemplified or specifically suggested herein. This includes proteins encoded by polynucleotides/DNA for use according to the subject invention.

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Ba131 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant toxins. Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Below is a listing of examples of amino acids belonging to each class.

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the Bt toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods is available for introducing a Bt gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. *Bacillus thuringiensis* or recombinant cells expressing the Bt toxins can be treated to prolong the toxin activity and stabilize the cell. The pesticide microcapsule that is formed comprises the Bt toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene or genes may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells producing the toxins of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores, crystals, and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant transformation. A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13 mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. Nos. 6,218,188 and 6,673,990. In addition, methods for creating synthetic Bt genes for use in plants are known in the art (Stewart and Burgin, 2007). One non-limiting example of a preferred transformed plant is a fertile maize plant comprising a plant-expressible gene encoding a Cry1Ab protein, and further comprising a second plant-expressible gene encoding a Vip3Ab protein.

Transfer (or introgression) of the Cry1Ab- and Vip3Ab-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1F- and Vip3Ab-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies. Roush et al., for example, outlines two-toxin strategies, also called "pyramiding" or "stacking," for management of insecticidal transgenic crops. (The Royal Society. *Phil. Trans. R. Soc. Lond. B*. (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a section of non-Bt crops/corn) for use with transgenic crops producing a single Bt protein active against target pests.

"The specific structured requirements for corn borer-protected Bt (Cry1Ab or Cry1F) corn products are as follows:

Structured refuges: 20% non-Lepidopteran Bt corn refuge in Corn Belt;

50% non-Lepidopteran Bt refuge in Cotton Belt

Blocks

Internal (i.e., within the Bt field)

External (i.e., separate fields within ½ mile (¼ mile if possible) of the   Bt field to maximize random mating)

In-field Strips

Strips must be at least 4 rows wide (preferably 6 rows) to reduce the effects of larval movement"

In addition, the National Corn Growers Association, on their website:

(ncga.com/insect-resistance-management-fact-sheet-bt-corn)

also provides similar guidance regarding the refuge requirements. For example:

"Requirements of the Corn Borer IRM:

Plant at least 20% of your corn acres to refuge hybrids

In cotton producing regions, refuge must be 50%

Must be planted within ½ mile of the refuge hybrids

Refuge can be planted as strips within the Bt field; the refuge strips must be at least 4 rows wide   Refuge may be treated with conventional pesticides only if economic thresholds are reached for target insect   Bt-based sprayable insecticides cannot be used on the refuge corn   Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three modes of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLES

Example 1

Summary of Examples

The following examples demonstrate that Vip3Ab1 has non-cross-resistant activity with Cry1Ab against corn earworm (CEW), thereby showing that these two proteins can counteract the development of resistance in CEW to either of these proteins alone.

We further demonstrated that Vip3Ab1 is active against *Plutella xylostella* (Linnaeus) (diamondback moth) larvae and against Cry1Ab-resistant *Plutella xylostella* (Linnaeus)

larvae. In a diet incorporation bioassay, Vip3Ab1 is toxic against both strains of this insect.

Further support for this resistance management is provided by radiolabeled competition binding studies using $^{125}$I Cry1Ab. Data is presented showing that $^{125}$I radio-labeled Cry1Ab binds strongly and specifically to a particular set of receptor proteins located in brush border membrane vesicle (BBMV) preparations from the midgut of *Heliothis zea* larvae. The binding of radioactive Cry1Ab to its receptors can be competitively displaced by using non-radioactive Cry1Ab in BBMV's from this insect. However, Vip3Ab1, either in its full length 85 kDa form, or when enzymatically processed by trypsin to a smaller molecular weight processed protein, does not displace the binding of $^{125}$I Cry1Ab from its receptors if this insect. These results show that Vip3Ab exerts its biological affect at a site different from where Cry1Ab binds.

Example 2

Purification and Trypsin Processing of Cry1Ab and Vip3Ab1 Proteins

The genes encoding the Cry1Ab and Vip3Ab1 pro toxins were expressed in *Pseudomonas fluorescens* expression strains and the full length proteins isolated as insoluble inclusion bodies. The washed inclusion bodies were solubilized by stirring at 37° C. in buffer containing 20 mM CAPS buffer, pH 11, +10 mM DDT, +0.1% 2-mercaptoethanol, for 2 hrs. The solution was centrifuged at 27,000×g for 10 min. at 37° C. and the supernatant treated with 0.5% (w/v) TCPK treated trypsin (Sigma). This solution was incubated with mixing for an additional 1 hr. at room temperature, filtered, then loaded onto a Pharmacia Mono Q 1010 column equilibrated with 20 mM CAPS pH 10.5. After washing the loaded column with 2 column volumes of buffer, the truncated toxin was eluted using a linear gradient of 0 to 0.5 M NaCl in 20 mM CAPS in 15 column volumes at a flow rate of 1.0 ml/min. Purified trypsin truncated Cry proteins eluted at about 0.2-0.3 M NaCl. The purity of the proteins was checked by SDS PAGE and with visualization using Coomassie brilliant blue dye. In some cases, the combined fractions of the purified toxin were concentrated and loaded onto a Superose 6 column (1.6 cm dia., 60 cm long), and further purified by size exclusion chromatography. Fractions comprising a single peak of the monomeric molecular weight were combined, and concentrated, resulting in a preparation more than 95% homogeneous for a protein having a molecular weight of about 60,000 kDa.

Processing of Vip3Ab1 was achieved in a similar manner starting with the purified full length 85 kDa protein (DIG-307). The protein (12 mg) was dialyzed into 50 mM sodium phosphate buffer, pH 8.4, then processed by adding 1 mg of solid trypsin and incubating for 1 hrs. at room temperature. The solution was loaded onto a MonoQ anion exchange column (1 cm dia., 10 cm. long), and eluted with a linear gradient of NaCl from 0 to 500 mM in 20 mM sodium phosphate buffer, pH 8.4 over 7 column volumes. Elution of the protein was monitored by SDS-PAGE. The major processed band had a molecular weight of 65 kDa, as determined by SDS-PAGE using molecular weight standards for comparison.

Example 3

Insect Bioassays

Purified proteins were tested for insecticidal activity in bioassays conducted with neonate *Plutella xylostella* (Linnaeus) and *Heliothis zea* larvae on artificial insect diet. The Cry1A-resistant *P. xylostella* were developed through a diet challenge regimen using a commercial Bt product (DiPel®) and derived from the NO-QA strain (Tabashnik et al., 1996; Tabashnik et al., 1997).

Insect bioassays were conducted in 128-well plastic bioassay trays (C-D International, Pitman, N.J.). Each well contained 0.5 mL of multi-species lepidoptera diet (Southland Products, Lake Village, Ark.). A 40 µL aliquot of the purified Cry or Vip3Ab1 protein diluted to various concentrations in 10 mM CAPS, pH 10.5, or control solution was delivered by pipette onto the 1.5 cm² diet surface of each well (26.7 µL/cm²). Sixteen wells were tested per sample. The negative control was a buffer solution blank containing no protein. Positive controls included preparations of Cry1Ac, or Cry1F. The treated trays were held in a fume hood until the liquid on the diet surface had evaporated or was absorbed into the diet.

Within a few hours of eclosion, individual larvae were picked up with a moistened camelhair brush and deposited on the treated diet, one larva per well. The infested wells were then sealed with adhesive sheets of clear plastic that are vented to allow gas exchange (C-D International, Pitman, N.J.). The bioassay trays were held under controlled environmental conditions (28° C., ~40% RH, 16:8 [L:D] photoperiod). After 5 days, the total number of insects exposed to each protein sample, the number of dead insects, and the weight of surviving insects were recorded.

Example 4

Iodination of Cry1Ab Toxins

Purified trypsin truncated Cry1Ab core toxin was iodinated using Iodo-Beads (Pierce). Briefly, two Iodo-Beads were washed twice with 500 µl of PBS (20 mM sodium phosphate, 0.15 M NaCl, pH 7.5), and placed into a 1.5 ml centrifuge tube behind lead shielding. To this was added 100 µl of PBS was added to the iodo-bead. In a hood and through the use of proper radioactive handling techniques, 0.5 mCi Na$^{125}$I (17.4 Ci/mg, Perkin Elmer) was added to the PBS solution with the Iodo-Bead. The components were allowed to react for 5 minutes at room temperature, then 5 µg of highly pure truncated Cry1Ab was added to the solution and allowed to react for an additional 3-5 minutes. The reaction was terminated by removing the solution from the iodo-bead and applying it to a desalting spin column (G-20, GE biosciences) equilibrated in 10 mM CAPS, pH 10.5. The iodo-bead was washed twice with 50 µl of PBS and the wash solution also applied to the desalting column. The radioactive solution was eluted through the desalting column by centrifugation at 1,000×g for 2 min. The $^{125}$I radiolabeled iodo-Cry1Ab was counted in a gamma counter for the amount of radioactivity, and the specific activity determined based upon an assumed 80% recovery of the input toxin.

Example 5

Preparation and Fractionation of Solubilized BBMV's

Standard methods of protein quantification and SDS-polyacrylamide gel electrophoresis were employed as taught, for example, in Sambrook et al. (Sambrook and Russell, 2001) and updates thereof. Last instar *H. zea* larvae were fasted overnight and then dissected after chilling on ice for 15 minutes. The midgut tissue was removed from the body cavity, leaving behind the hindgut attached to the integument. The midgut was placed in a 9× volume of ice cold homogenization buffer (300 mM mannitol, 5 mM EGTA, 17 mM Tris base, pH7.5), supplemented with Protease Inhibitor Cocktail (Sigma-Aldrich P-2714) diluted as recommended by the supplier. The tissue was homogenized with 15 strokes of a glass tissue homogenizer. BBMV's were prepared by the $MgCl_2$ precipitation method of Wolfersberger (Wolfersberger, 1993). Briefly, an equal volume of a 24 mM $MgCl_2$ solution in 300 mM mannitol was mixed with the midgut homogenate, stirred for 5 minutes and allowed to stand on ice for 15 min. The solution was centrifuged at 2,500×g for 15 min at 4° C. The supernatant was saved and the pellet suspended into the original volume of 0.5× diluted homogenization buffer and centrifuged again. The two supernatants were combined and centrifuged at 27,000×g for 30 min at 4° C. to form the BBMV fraction. The pellet was suspended into BBMV Storage Buffer (10 mM HEPES, 130 mM KCl, 10% glycerol, pH 7.4) to a concentration of about 3 mg/ml protein. Protein concentration was determined using BSA as the standard.

L-leucine-p-nitroanilide aminopeptidase activity (a marker enzyme for the BBMV fraction) was determined prior to freezing the samples. Briefly, 50 μl of L-leucine-p-nitroanilide (1 mg/ml in PBS) was added to 940 ml 50 mM Tris HCl in a standard cuvette. The cuvette was placed in a Cary 50 Bio spectrophotometer, zeroed for absorbance reading at 405 nm, and the reaction initiated by adding 10 μl of either insect midgut homogenate or insect BBMV preparation. The increase in absorbance at 405 nm was monitored for 5 minutes at room temperature. The specific activity of the homogenate and BBMV preparations was determined based upon the kinetics of the absorbance increase over time during a linear increase in absorbance per unit total protein added to the assay based upon the following equation:

$$\Delta OD/(min*mg) = \text{Aminopeptidase Rate} (\Delta OD/ml*min)/[\text{protein}] (mg/ml)$$

The specific activity of this enzyme typically increased 7-fold compared to that found in the starting midgut homogenate fraction. The BBMV's were aliquoted into 250 μl samples, flash frozen in liquid $N_2$ and stored at −80° C.

Example 6

Electrophoresis

Analysis of proteins by SDS-PAGE was conducted under reducing (i.e. in 5% β-mercaptoethanol, BME) and denaturing (i.e. heated 5 minutes at 90° in the presence of 4% SDS) conditions. Proteins were loaded into wells of a 4% to 20% tris-glycine polyacrylamide gel (BioRad; Hercules, Calif.) and separated at 200 volts for 60 minutes. Protein bands were detected by staining with Coomassie Brilliant Blue R-250 (BioRad) for one hour, and destained with a solution of 5% methanol in 7% acetic acid. The gels were imaged and analyzed using a BioRad Fluoro-S Multi Imager™. Relative molecular weights of the protein bands were determined by comparison to the mobilities of known molecular weight proteins observed in a sample of BenchMark™ Protein Ladder (Invitrogen, Carlsbad, Calif.) loaded into one well of the gel.

Example 7

Binding of $^{125}$I-Labeled Cry1Ab to BBMV's from *H. zea* Larvae

A saturation curve was generated to determine the optimal amount of BBMV protein to use in the Cry core toxin protein binding assays. 0.5 nM of $^{125}$I-radiolabeled Cry1Ab core toxin protein was incubated for 1 hr at 28° in binding buffer (8 mM $NaHPO_4$, 2 mM $KH_2PO_4$, 150 mM NaCl, 0.1% BSA, pH7.4) with amounts of BBMV protein ranging from 0 μg/mL to 500 μg/mL (total volume of 0.5 mL). $^{125}$I-labeled Cry core toxin protein bound to the BBMV proteins was separated from the unbound fraction by sampling 150 μL of the reaction mixture in triplicate into separate 1.5 mL centrifuge tubes and centrifuging the samples at 14,000×g for 8 minutes at room temperature. The supernatant was gently removed and the pellet was washed three times with ice cold binding buffer. The bottom of the centrifuge tube containing the pellet was cut off, placed into a 13×75-mm glass culture tube and the samples were counted for 5 minutes each in the gamma counter. CPM (counts per minute) obtained minus background CPM (reaction with no BBMV protein) was plotted versus BBMV protein concentration. The optimal concentration of BBMV protein to use in the binding assay was determined to be 150 μg/mL.

Homologous and heterologous competition binding assays were conducted using 150 μg/mL BBMV protein and 0.5 nM of the $^{125}$I-radiolabeled Cry core toxin protein. Concentrations of the competitive non-radiolabeled Cry core toxin protein added to the reaction mixture ranged from 0.045 nM to 1000 nM and were added at the same time as the radioactive Cry core toxin protein, to assure true binding competition. Incubations were carried out for 1 hr at 28° and the amount of $^{125}$I-labeled Cry core toxin protein bound to the BBMV (total binding) was measured as described above. Non-specific binding was represented by the counts obtained in the presence of 1,000 nM of the homologous non-radiolabeled Cry core toxin protein. Specific binding was measured by subtracting the level of non-specific binding obtained from total binding. One hundred percent specific binding was considered to be the amount of binding obtained in the absence of any competitor ligand minus the amount of binding obtained in the presence of 1,000 nM of the homologous non-radiolabeled Cry core toxin protein. The amount of displacement by heterologous ligands was compared to 100% specific binding of $^{125}$I Cry1Ab to its receptor.

Example 8

Summary of Results

Figure 1:
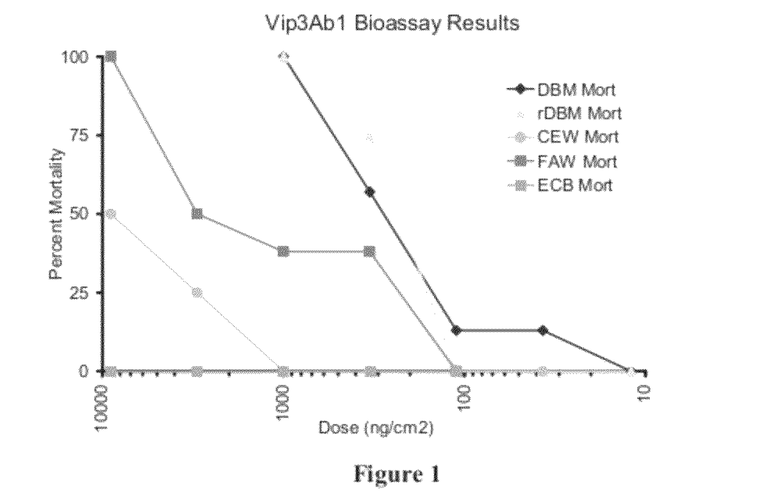
FIG. 1. Mortality dose response of full length Vip3Ab1 against *Plutella xylostella* (Linnaeus) (DBM), and Cry1A resistant *Plutella xylostella* (rDBM), *Heliothis zea* (CEW), *Spodoptera frugiperda* (J. E. Smith), (FAW) and *Ostrinia nubilalis* (Hübner), (ECB) larvae when the purified toxin is applied topically to an artificial insect diet. Percent mortality is based upon a reading taken 5 days after exposure to toxin on 8 insects per dose.
Figure 2:
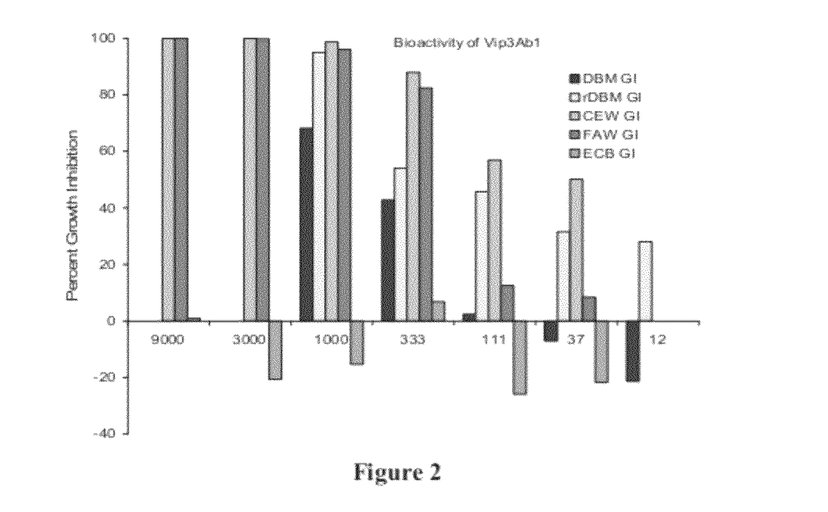
FIG. 2. Growth inhibition dose response of full length Vip3Ab1 against *Plutella xylostella* (Linnaeus) (DBM), and Cry1A resistant *Plutella xylostella* (rDBM), *Heliothis zea* (CEW), *Spodoptera frugiperda* (J. E. Smith), (FAW) and *Ostrinia nubilalis* (Hübner), (ECB) larvae when the purified toxin is applied topically to an artificial insect diet. Percent growth inhibition is based upon comparison of average weight of 8 larvae treated with buffer only to the weight of larvae exposed to toxin for 5 days.

Mortality results from bioassays of the full length Vip3Ab1 protein tested at a variety of doses against wild type and Cry1A resistant *P. xylostella* larvae, and *H. zea* larvae are shown in FIG. 1. Percent growth inhibition results of the bioassays are plotted in FIG. 2. Concentrations of Vip3Ab1 tested were 9,000, 3,000, 1,000, 333, 111, 37, and 12 ng/cm². The toxin was most active against *P. xylostella* larvae, showing an equivalent mortality dose response for both the wild type and Cry1Ab resistant larvae. The LC-50 for *P. xylostella* was about 200 ng/cm². Growth inhibition was observed against *H. zea* larvae, although higher concentrations were required to result in mortality in the time period of the assay. The high level of growth inhibition observed against *H. zea* larvae suggests that these insects would most likely progress to mortality if left for a longer time period.

Radiolabeled competition binding assays were conducted to determine if trypsin truncated Vip3Ab1 competes with the binding of $^{125}$I radiolabeled Cry1Ab receptor proteins contained in BBMV's *H. zea*.

Figure 3:
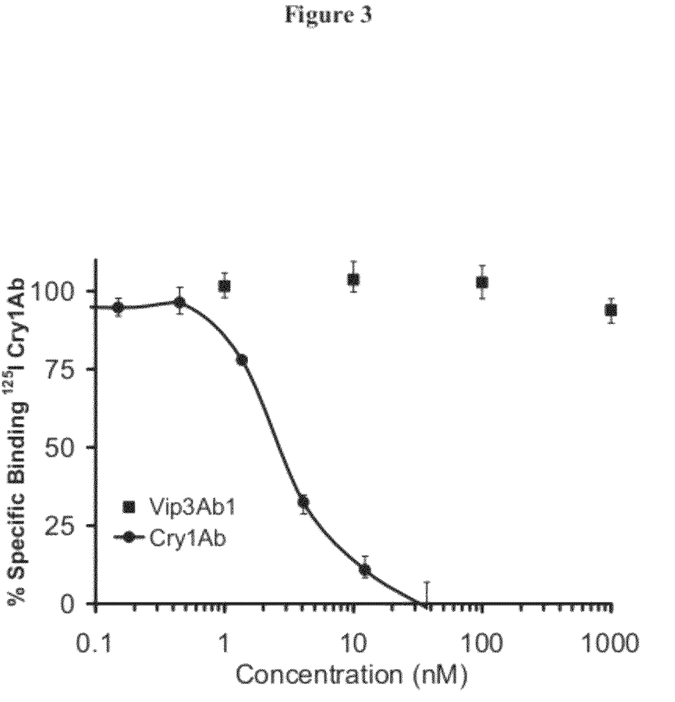
FIG. 3. Competitive displacement curves for binding of $^{125}$I Cry1Ab to BBMV protein prepared from *H. zea*. BBMV concentration was 0.10 mg protein/ml, and $^{125}$I Cry1Ab was 0.25 nM. 100% percent specific binding of $^{125}$I Cry1Ab was measured as total binding in the absence of non-labeled Cry1Ab minus non-specific binding measured in the presence of 500 nM Cry1Ab. Vip3Ab1 was tested at concentrations as high as 1,000 nM (4,000-fold higher that the radiolabeled displacement ligand) and did not displace the binding of $^{125}$I Cry1Ab. Non-radiolabeled displaced $^{125}$I Cry1Ab by 50% at about 2 nM.

Experiments were conducted comparing the ability of Vip3Ab1 to compete with the binding of $^{125}$I Cry1Ab in BBMV's prepared from *H. zea* larvae (FIG. 3). In the BBMV preparations, non-radiolabeled Cry1Ab was shown to effectively compete off the binding of $^{125}$I Cry1Ab from the *H. zea* BBMV proteins, but Vip3Ab1 did not result in any displacement of the radiolabeled Cry1Ab ligand from these BBMV preparations. These three studies demonstrate that Vip3Ab1 does not compete with the binding of Cry1Ab in *H. zea* larvae.

Insects can develop resistance to the toxicity of Cry proteins through a number of different biochemical mechanisms, but the most common mechanism is due to a reduction in the ability of the Cry toxin protein to bind to its specific receptor in the gut of the insect (Heckel et al., 2007; Tabashnik et al., 2000; Xu et al., 2005). This can be brought about thought small point mutations, large gene deletions, or though other genetic or biochemical mechanisms.

Vip3Ab1 complements the activity of Cry1Ab, in that it has biological activity against similar insects, yet does not bind to the same receptor sites as these Cry proteins, and thus is not affected by resistance mechanisms that would involve reduction of Cry toxin binding. We concluded from these studies that Vip3Ab1 is an excellent insect toxin to combine with Cry1Ab as an insect resistance management approach to provide biological activity against insects that may have developed resistance to either one of these proteins, and also to prevent the survival of Cry1A resistant insects. Since Vip3Ab1 is toxic to Cry1A-resistant insects, this toxin would be an excellent stacking partner to combine with Cry1Ab to deliver activity against both wild type and resistant insects.

REFERENCE LIST

Heckel, D. G., Gahan, L. J., Baxter, S. W., Zhao, J. Z., Shelton, A. M., Gould, F., and Tabashnik, B. E. (2007). The diversity of Bt resistance genes in species of Lepidoptera. J Invertebr Pathol 95, 192-197.

Luo, K., Banks, D., and Adang, M. J. (1999). Toxicity, binding, and permeability analyses of four *bacillus thuringiensis* cry1 delta-endotoxins using brush border membrane vesicles of *spodoptera exigua* and *spodoptera frugiperda*. Appl. Environ. Microbiol. 65, 457-464.

Palmer, M., Buchkremer, M, Valeva, A, and Bhakdi, S. Cysteine-specific radioiodination of proteins with fluorescein maleimide. Analytical Biochemistry 253, 175-179. 1997. Ref Type: Journal (Full)

Sambrook, J. and Russell, D. W. (2001). Molecular Cloning: A Laboratory Manual. Cold Spring Harbor Laboratory).

Schlenz, M. L., Babcock, J. M., and Storer, N. P. Response of Cry1F-resistant and Susceptible European Corn Borer and Fall Armyworm Colonies to Cry1A. 105 and Cry12Ab2. DAI 0830, 2008. Indianapolis, Dow AgroSciences. Derbi Report.

Sheets, J. J. and Storer, N. P. Analysis of Cry1Ac Binding to Proteins in Brush Border Membrane Vesicles of Corn Earworm Larvae (*Heleothis zea*). Interactions with Cry1F Proteins and Its Implication for Resistance in the Field. DAI-0417, 1-26. 2001. Indianapolis, Dow AgroSciences.

Tabashnik, B. E., Liu, Y. B., Finson, N., Masson, L., and Heckel, D. G. (1997). One gene in diamondback moth confers resistance to four *Bacillus thuringiensis* toxins. Proc. Natl. Acad. Sci. U.S. A 94, 1640-1644.

Tabashnik, B. E., Malvar, T., Liu, Y. B., Finson, N., Borthakur, D., Shin, B. S., Park, S. H., Masson, L., de Maagd, R. A., and Bosch, D. (1996). Cross-resistance of the diamondback moth indicates altered interactions with domain II of *Bacillus thuringiensis* toxins. Appl. Environ. Microbiol. 62, 2839-2844.

Tabashnik, B. E., Roush, R. T., Earle, E. D., and Shelton, A. M. (2000). Resistance to Bt toxins. Science 287, 42.

Wolfersberger, M. G. (1993). Preparation and partial characterization of amino acid transporting brush border membrane vesicles from the larval midgut of the gypsy moth (*Lymantria dispar*). Arch. Insect Biochem. Physiol 24, 139-147.

Xu, X., Yu, L., and Wu, Y. (2005). Disruption of a cadherin gene associated with resistance to Cry1Ac {delta}-endotoxin of *Bacillus thuringiensis* in *Helicoverpa armigera*. Appl Environ Microbiol 71, 948-954.

We claim:

1. A transgenic plant comprising DNA encoding a Vip3Ab insecticidal protein and DNA encoding a Cry1Ab insecticidal protein, wherein said Cry1Ab insecticidal protein comprises SEQ ID NO:2 and said Vip3Ab insecticidal protein comprises SEQ ID NO:1.

2. Seed of the plant of claim 1, wherein said seed comprises said DNA encoding said Vip3Ab insecticidal protein and DNA encoding said Cry1Ab insecticidal protein.

3. The plant of claim 1 wherein said DNA was introgressed into said plant.

4. Seed of the plant of claim 3, wherein said seed contains DNA encoding said Vip3Ab insecticidal protein and DNA encoding said Cry1Ab insecticidal protein.

5. A plurality of transgenic plants of claim 1 in a field of plants comprising non-Bt refuge plants and said transgenic plants, wherein said refuge plants comprise less than 40% of all crop plants in said field.

6. The plants of claim 5, wherein said refuge plants comprise less than 30% of all the crop plants in said field.

7. The plants of claim 5, wherein said refuge plants comprise less than 20% of all the crop plants in said field.

8. The plants of claim 5, wherein said refuge plants comprise less than 10% of all the crop plants in said field.

9. The plants of claim 5, wherein said refuge plants comprise less than 5% of all the crop plants in said field.

10. The plants of claim 5, wherein said refuge plants are in blocks or strips.

11. A mixture of seeds comprising refuge seeds from non-Bt refuge plants, and a plurality of seeds of claim 2, wherein said refuge seeds comprise less than 40% of all the seeds in the mixture.

12. The mixture of seeds of claim 11, wherein said refuge seeds comprise less than 30% of all the seeds in the mixture.

13. The mixture of seeds of claim 11, wherein said refuge seeds comprise less than 20% of all the seeds in the mixture.

14. The mixture of seeds of claim 11, wherein said refuge seeds comprise less than 10% of all the seeds in the mixture.

15. The mixture of seeds of claim 11, wherein said refuge seeds comprise less than 5% of all the seeds in the mixture.

16. A method of managing development of resistance by *Helicoverpa zea* insects to an insecticidal protein derived from a *Bacillus thuringiensis*, said method comprising planting seeds to produce the plants of claim 5.

17. A composition for controlling *Helicoverpa zea* insects that are resistant to a Cry protein, said composition comprising cells that express effective amounts of both a Cry1Ab insecticidal protein and a Vip3Ab insecticidal protein.

18. The composition of claim 17 comprising a host transformed to express both a Cry1Ab insecticidal protein and a Vip3Ab insecticidal protein, wherein said host is a microorganism or a plant cell.

19. A method of controlling *Helicoverpa zea* insects that are resistant to a Cry protein said method comprising presenting to said insects an effective amount of the composition of claim 17.

20. The plants of claim 5, wherein said plants occupy more than 10 acres.

21. The plant of claim 1, wherein said plant is selected from the group consisting of corn, soybeans, and cotton.

22. The plant of claim 1, wherein said plant is a maize plant.

23. A plant cell of the plant of claim 1, wherein said plant cell comprises said DNA encoding said Cry1Ab insecticidal protein and said DNA encoding said Vip3Ab insecticidal protein, wherein said Cry1Ab insecticidal protein is SEQ ID NO:2 and said Vip3Ab insecticidal protein is SEQ ID NO:1.

24. A plant cell comprising DNA encoding a Vip3Ab insecticidal protein having SEQ ID NO: 1 and DNA encoding a Cry1Ab insecticidal protein having SEQ ID NO:2.

\* \* \* \* \*

SEQUENCE LISTING

```
<160> NUMBER OF SEQ ID NOS: 2

<210> SEQ ID NO 1
<211> LENGTH: 787
<212> TYPE: PRT
<213> ORGANISM: Artificial Sequence
<220> FEATURE:
<223> OTHER INFORMATION: VIP3Ab

<400> SEQUENCE: 1

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95
```

```
Asn Gln Val Leu Asn Asp Val Asn Asn Lys Leu Asp Ala Ile Asn Thr
                100                 105                 110
Met Leu His Ile Tyr Leu Pro Lys Ile Thr Ser Met Leu Ser Asp Val
        115                 120                 125
Met Lys Gln Asn Tyr Ala Leu Ser Leu Gln Val Glu Tyr Leu Ser Lys
    130                 135                 140
Gln Leu Lys Glu Ile Ser Asp Lys Leu Asp Val Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
        180                 185                 190
Thr Leu Lys Val Lys Lys Asp Ser Ser Pro Ala Asp Ile Leu Asp Glu
    195                 200                 205
Leu Thr Glu Leu Thr Glu Leu Ala Lys Ser Val Thr Lys Asn Asp Val
210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Ala Lys Glu Asn Val Lys Thr Ser Gly Ser Glu Val Gly Asn Val Tyr
        260                 265                 270
Asn Phe Leu Ile Val Leu Thr Ala Leu Gln Ala Lys Ala Phe Leu Thr
    275                 280                 285
Leu Thr Thr Cys Arg Lys Leu Leu Gly Leu Ala Asp Ile Asp Tyr Thr
290                 295                 300
Ser Ile Met Asn Glu His Leu Asn Lys Glu Lys Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
        340                 345                 350
Pro Gly His Ala Leu Val Gly Phe Glu Ile Ser Asn Asp Ser Met Thr
    355                 360                 365
Val Leu Lys Val Tyr Glu Ala Lys Leu Lys Gln Asn Tyr Gln Val Asp
370                 375                 380
Lys Asp Ser Leu Ser Glu Val Ile Tyr Ser Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
        420                 425                 430
Thr Leu Arg Tyr Glu Val Thr Ala Asn Ser Tyr Asp Ser Ser Thr Gly
    435                 440                 445
Glu Ile Asp Leu Asn Lys Lys Val Glu Ser Glu Ala Glu Tyr
450                 455                 460
Arg Thr Leu Ser Ala Asn Asn Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
        500                 505                 510
Glu Leu Leu Leu Ala Thr Asp Leu Ser Asn Lys Glu Thr Lys Leu Ile
```

```
            515                 520                 525
Val Pro Pro Ile Ser Phe Ile Ser Asn Ile Val Glu Asn Gly Asn Leu
530                 535                 540

Glu Gly Glu Asn Leu Glu Pro Trp Ile Ala Asn Asn Lys Asn Ala Tyr
545                 550                 555                 560

Val Asp His Thr Gly Ile Asn Gly Thr Lys Val Leu Tyr Val His
                565                 570                 575

Lys Asp Gly Glu Phe Ser Gln Phe Val Gly Gly Lys Leu Lys Ser Lys
                580                 585                 590

Thr Glu Tyr Val Ile Gln Tyr Ile Val Lys Gly Lys Ala Ser Ile Tyr
                595                 600                 605

Leu Lys Asp Lys Lys Asn Glu Asn Ser Ile Tyr Glu Glu Ile Asn Asn
610                 615                 620

Asp Leu Glu Gly Phe Gln Thr Val Thr Lys Arg Phe Ile Thr Gly Thr
625                 630                 635                 640

Asp Ser Ser Gly Ile His Leu Ile Phe Thr Ser Gln Asn Gly Glu Gly
                645                 650                 655

Ala Phe Gly Gly Asn Phe Ile Ile Ser Glu Ile Arg Thr Ser Glu Glu
                660                 665                 670

Leu Leu Ser Pro Glu Leu Ile Met Ser Asp Ala Trp Val Gly Ser Gln
                675                 680                 685

Gly Thr Trp Ile Ser Gly Asn Ser Leu Thr Ile Asn Ser Asn Val Asn
690                 695                 700

Gly Thr Phe Arg Gln Asn Leu Pro Leu Glu Ser Tyr Ser Thr Tyr Ser
705                 710                 715                 720

Met Asn Phe Thr Val Asn Gly Phe Gly Lys Val Thr Val Arg Asn Ser
                725                 730                 735

Arg Glu Val Leu Phe Glu Lys Ser Tyr Pro Gln Leu Ser Pro Lys Asp
                740                 745                 750

Ile Ser Glu Lys Phe Thr Thr Ala Ala Asn Asn Thr Gly Leu Tyr Val
                755                 760                 765

Glu Leu Ser Arg Ser Thr Ser Gly Gly Ala Ile Asn Phe Arg Asp Phe
770                 775                 780

Ser Ile Lys
785

<210> SEQ ID NO 2
<211> LENGTH: 1155
<212> TYPE: PRT
<213> ORGANISM: Artificial Sequence
<220> FEATURE:
<223> OTHER INFORMATION: Cry1AB

<400> SEQUENCE: 2

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
                35                  40                  45

Glu Phe Val Pro Gly Ala Gly Phe Val Leu Gly Leu Val Asp Ile Ile
                50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
```

```
                     85                  90                  95
Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510
```

```
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
        530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
                580                 585                 590
Ser Gly Asn Glu Val Tyr Ile Asp Arg Ile Glu Phe Val Pro Ala Glu
        595                 600                 605
Val Thr Phe Glu Ala Glu Tyr Asp Leu Glu Arg Ala Gln Lys Ala Val
        610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
                660                 665                 670
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
        690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Leu Thr Tyr Leu Tyr Gln
                725                 730                 735
Lys Ile Asp Glu Ser Lys Leu Lys Ala Tyr Thr Arg Tyr Gln Leu Arg
                740                 745                 750
Gly Tyr Ile Glu Asp Ser Gln Asp Leu Glu Ile Tyr Leu Ile Arg Tyr
        755                 760                 765
Asn Ala Lys His Glu Thr Val Asn Val Pro Gly Thr Gly Ser Leu Trp
        770                 775                 780
Arg Leu Ser Ala Pro Ser Pro Ile Gly Lys Cys Ala His His Ser His
785                 790                 795                 800
His Phe Ser Leu Asp Ile Asp Val Gly Cys Thr Asp Leu Asn Glu Asp
                805                 810                 815
Leu Gly Val Trp Val Ile Phe Lys Ile Lys Thr Gln Asp Gly His Ala
                820                 825                 830
Arg Leu Gly Asn Leu Glu Phe Leu Glu Glu Lys Pro Leu Val Gly Glu
        835                 840                 845
Ala Leu Ala Arg Val Lys Arg Ala Glu Lys Lys Trp Arg Asp Lys Arg
        850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Ala Asp Lys Arg Val His Ser
                900                 905                 910
Ile Arg Glu Ala Tyr Leu Pro Glu Leu Ser Val Ile Pro Gly Val Asn
        915                 920                 925
```

-continued

```
Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Gln Asn
            965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005

Ala Tyr Lys Glu Gly Tyr Gly Glu Gly Cys Val Thr Ile His Glu
    1010                1015                1020

Ile Glu Asn Asn Thr Asp Glu Leu Lys Phe Ser Asn Cys Val Glu
    1025                1030                1035

Glu Glu Val Tyr Pro Asn Asn Thr Val Thr Cys Asn Asp Tyr Thr
    1040                1045                1050

Ala Thr Gln Glu Glu Tyr Glu Gly Thr Tyr Thr Ser Arg Asn Arg
    1055                1060                1065

Gly Tyr Asp Gly Ala Tyr Glu Ser Asn Ser Ser Val Pro Ala Asp
    1070                1075                1080

Tyr Ala Ser Ala Tyr Glu Glu Lys Ala Tyr Thr Asp Gly Arg Arg
    1085                1090                1095

Asp Asn Pro Cys Glu Ser Asn Arg Gly Tyr Gly Asp Tyr Thr Pro
    1100                1105                1110

Leu Pro Ala Gly Tyr Val Thr Lys Glu Leu Glu Tyr Phe Pro Glu
    1115                1120                1125

Thr Asp Lys Val Trp Ile Glu Ile Gly Glu Thr Glu Gly Thr Phe
    1130                1135                1140

Ile Val Asp Ser Val Glu Leu Leu Leu Met Glu Glu
    1145                1150                1155
```